(12) United States Patent
Stoppini (10) Patent No.: US 7,897,377 B2
(45) Date of Patent: Mar. 1, 2011

(54) CELL- AND TISSUE CULTURE DEVICE

(75) Inventor: Luc Stoppini, Geneva (CH)

(73) Assignee: Capsant Neurotechnologies, S.A. (CH)

( * ) Notice: Subject to any disclaimer, the term of this patent is extended or adjusted under 35 U.S.C. 154(b) by 73 days.

(21) Appl. No.: 11/922,253

(22) PCT Filed: Jun. 15, 2006

(86) PCT No.: PCT/IB2006/001160
§ 371 (c)(1),
(2), (4) Date: Dec. 14, 2007

(87) PCT Pub. No.: WO2006/134432
PCT Pub. Date: Dec. 21, 2006

(65) Prior Publication Data
US 2009/0137032 A1    May 28, 2009

(30) Foreign Application Priority Data
Jun. 15, 2005   (GB) .................................. 0512216.3

(51) Int. Cl.
*A01N 1/00* (2006.01)
*A01N 1/02* (2006.01)

(52) U.S. Cl. ................ 435/284.1; 435/173.5; 435/297.1; 435/297.5

(58) Field of Classification Search ............... 435/173.4, 435/297.5, 284.1; 239/6, 37, 55, 56, 59
See application file for complete search history.

(56) References Cited

U.S. PATENT DOCUMENTS

| 4,154,795 A | 5/1979 | Thorne |
| 4,324,859 A * | 4/1982 | Saxholm .................... 435/33 |
| 4,908,236 A | 3/1990 | Pitt et al. |

(Continued)

FOREIGN PATENT DOCUMENTS

EP    1078982 A2    2/2001

(Continued)

OTHER PUBLICATIONS

Beaupain, et al., 'A method for three-dimensional coculture of cancer cells combined to any other type of cells maintained organotypically,' *Methods in Cell Science*, 21(1):2-30 (1999).

(Continued)

*Primary Examiner* — William H Beisner
*Assistant Examiner* — Michael Hobbs
(74) *Attorney, Agent, or Firm* — Dean W. Russell; Kilpatrick Townsend & Stockton LLP (57) ABSTRACT

The present invention relates to the field of cell and tissue culture. In particular, the invention provides a novel device for organotypic culture. The device comprises a medium conduit having one open end and one end closed by a porous membrane fused across it; and a frame holding the medium conduit in a substantially vertical orientation; wherein the medium conduit is adapted to permit retention by capillarity of a sufficient volume of liquid culture medium in the medium conduit to contact the surface of the porous membrane and thus supply nutrients to cells that may be grown on the porous membrane. The device may further comprise a cell suspension conduit having one end open and one end closed by the surface of said porous membrane contralateral to the surface of said porous membrane sealed to said medium conduit; wherein said frame holds the medium conduit and the cell suspension conduit in a substantially vertical orientation.

21 Claims, 6 Drawing Sheets

U.S. PATENT DOCUMENTS

| | | | | |
|---|---|---|---|---|
| 5,583,037 | A | * | 12/1996 | Mussi et al. ............... 435/396 |
| 5,834,312 | A | | 11/1998 | Wille, Jr. |
| 6,043,027 | A | * | 3/2000 | Selick et al. .................. 435/4 |
| 6,517,856 | B1 | * | 2/2003 | Roe et al. .................... 424/410 |
| 6,689,594 | B1 | | 2/2004 | Hanni et al. |
| 2004/0151729 | A1 | | 8/2004 | Michalopoulos et al. |
| 2004/0175367 | A1 | | 9/2004 | Herlyn et al. |
| 2005/0226784 | A1 | * | 10/2005 | Kobayashi .................... 422/101 |

FOREIGN PATENT DOCUMENTS

| | | |
|---|---|---|
| EP | 1205541 A1 | 5/2002 |
| EP | 1367119 A2 | 12/2003 |
| JP | 3147782 | 6/1991 |
| WO | WO 96/21851 | 7/1996 |
| WO | WO 97/04074 | 2/1997 |
| WO | WO 99/58042 | 11/1999 |
| WO | WO 99/64559 | 12/1999 |
| WO | WO 2004/007699 A2 | 1/2004 |
| WO | WO 2005/107642 | 11/2005 |
| WO | WO 2006/136953 | 12/2006 |

OTHER PUBLICATIONS

Becker-Hapak, et al., 'TAT-mediated protein transduction into mammalian cells,' *Methods*, 24:247-256 (2001).

Buchs, et al., 'Structural modifications associated with synaptic development in area CA1 of rat hippocampal organotypic cultures,' *Developmental Brain Res.*, 71:81-91 (1993).

Chatterjee, 'The effect of culture on ultrastructure of dissociated rabbit adenobypophysial cells,' *J. Anat.* 121(2):241-258 (1975).

Corradino, 'Embryonic chick intestine in organ culture. A unique system for the study of the intestinal calcium absorptive mechanism,' *J. Cell. Biol.*, 58:64-78 (1973).

Douglas, et al., 'Organotypic Culture of Dissociated Fetal Rat Lung Cells on a Collagen Sponge Matrix,' TCA (Tissue Culture Association) Manual, 4(1):749-753 (1978).

Fawcett, et al., 'Dopaminergic neuronal survival and the effects of bFGF in explant, three dimensional and monolayer cultures of embryonic rat ventral mesencephalon,' *Exp. Brain Res.*, 106:275-282 (1995).

Feng, 'Imaging neuronal subsets in transgenic mice expressing multiple spectral variants of GFP,' *Neuron*, 28:41-51 (2000).

Honegger, et al., 'Aggregating Neural Cell Cultures,' in *Protocols for Neural Cell Culture* (Federoff and Richardson, Editors) Third Edition, Humana Press, Totowa, NJ, USA, ISBN 1-59259-207-4, pp. 199-218 (2001).

Kalabis, et al., 'Stimulation of human colonic epithelial cells by leukemia inhibitory factor is dependent on collagen-embedded fibroblasts in organotypic culture,' *FASEB, J.*, 17:1115-1117 (2003).

Mazurkiewicz, et al., 'Organotypic Cultures of the Avian Salt Gland Biosynthesis of Membrane Proteins,' Journal of Cell Science, 48:75-88 (1981).

Michalopoulos, et al., 'Histological organization in hepatocyte organoid cultures,' *Am. J. Pathol.*, 159:1877-1887 (2001).

Muller, et al., 'Interface Organotypic Hippocampal Slice Cultures,' *Protocols for Neural Cell Culture*, 3rd Edition, Federoff and Richardson, Editors, pp. 13-27 (2001).

Mummery, et al., 'Cardiomyocyte differentiation of mouse and human embryonic stem cells,' *J. Anat.*, 200:233-242 (2002).

Piper, et al., 'Novel SOX9 expression during human pancreas development correlates to abnormalities in Campomelic dysplasia,' *Mech. Dev.*, 116:223-226 (2002).

Ren, et al., Altered inotropic response to insulin-like growth factor I in diabetic rat heart: influence of intracellular $Ca^{2+}$ and nitric oxide, *Am. J. Physiol.*, 275:H823-H830 (1998).

Rochkind, et al., 'Transplantation of embryonal spinal cord nerve cells cultured on biodegradable microcarriers followed by low power laser irradiation for the treatment of traumatic paraplegia in rats,' *Neural Res.*, 24:355-360 (2002).

Smith, et al., 'Measurement of protein using bicinchoninic acid,' *Anal. Biochem.*, 150:76-85 (1985).

Stoppini, et al., Lesion-induced neurite sprouting and synapse formation in hippocampal organotypic cultures. *Neuroscience*, 57(4):985-994 (1993).

Stoppini, et al., 'A simple method for organotypic cultures of nervous tissue,' *Neurosci. Methods*, 37:173-182 (1991).

Turnpenny, et al., 'Derivation of human embryonic germ cells: an alternative source of pluripotent stem cells,' *Stem Cells*, 21:598-609 (2003).

Verrill, et al., Organotypic liver culture in a fluid-air interface using slices of neonatal rat and adult human tissue—a model of fibrosis in vitro, *J. Pharmacol. Toxicol. Methods*, 48:103-110 (2002).

Wicks, 'Induction of tyrosine-alphaketoglutarate transaminase in fetal rat liver,' *J. Biol. Chem.*, 243:900-906 (1968).

Wildenthal, 'Long-term maintenance of spontaneously beating mouse hearts in organ culture,' J. Appl. Physiol., 30:153-157 (1971).

* cited by examiner

CELL- AND TISSUE CULTURE DEVICE

CROSS REFERENCE TO RELATED APPLICATIONS

This application is the U.S. national phase of International Application No. PCT/IB2006/001160 filed on Jun. 15, 2006 and published in English on Dec. 21, 2006 as International Publication No. WO 2006/134432 A2, which application claims priority to Great Britain Patent Application No. 0512216.3 filed on Jun. 15, 2005, the contents of which are incorporated herein by reference.

The invention relates to the field of cell and tissue culture. In particular, the invention provides a novel device for organotypic culture.

Tissue culture is the ex vivo maintenance of cells that originated from an organ or tissue of an animal or plant organism. Methods of tissue culture have been developed and improved over many decades.

The culture of cells obtained directly from a plant or animal organ or tissue is called primary culture. According to one method of primary culture, organ explants are placed in a suitable sterile culture medium in a suitable culture vessel provided with a sterile atmosphere of suitable composition, such that cells grow from the edges of the explant. Another approach to primary culture is to dissociate the cells of the organ or tissue by enzymatic and/or mechanical treatment and culture dissociated cells in an appropriate environment as described above.

One disadvantage of primary cultures of animal cells is that the cells only have a limited lifespan. Cells in primary culture may undergo cell division but they usually do so only a limited number of times before undergoing a form of cell death called senescence. A further disadvantage of explant-based animal cell primary culture is that the cultured cells usually lose many of the characteristics that are typical of cells in the source organ in vivo, unless specific steps are taken to prevent such loss of characteristics. The loss of in vivo characteristics during explant-based or dissociated cell-based primary culture and the emergence of immortal cell lines has major implications for biological and medical research and product development because it means that such primary cell cultures cannot be used to predict in vivo responses accurately. As a result, many biological tests to assess the safety and efficacy of candidate drugs must be carried out in vivo in whole animals. Such tests in whole animals are expensive, leading to higher healthcare costs, and may compromise animal welfare. For many years, there has therefore been considerable impetus to develop in vitro tests which more accurately predict an in vivo response.

Organ culture is the maintenance of all or part of an animal organ ex vivo, under conditions which sustain the life and function of the organ for a period of time. For example, there are established procedures to culture liver (Wicks W., 1968), heart (Wildenthal K., 1971) and intestine (Corradino R., 1973). Organ culture has a major advantage over explant-based primary cell cultures and cell lines in that most or all of the physiological properties of the organ are maintained. However, the throughput of organ culture is limited by the manipulations necessary to remove the organ surgically from the host and set up the culture system. Furthermore, only one, two or a few cultures can be obtained per donor animal. These limitations render organ culture too slow and costly for drug screening and drug target screening, together with many other applications in biological research.

A major advance in the field of tissue culture has been the introduction of organotypic culture methods for organ and tissue slices. Thin (50-500 µm) slices of an animal organ are cultured under conditions in which the slices retain the cellular composition, morphology and the physiological properties of the source organ. The conditions in which the organ slices are cultured are critical to achieve organotypic culture. The organ slices are cultured on the upper surface of a porous membrane and supplied with nutrient from the lower surface of said porous membrane such that the organ slice is not fully immersed but is covered only by a thin film of culture medium (Stoppini L. et al, 1991).

Gas transfer to the slice, both for the uptake of oxygen and the removal of carbon dioxide, is much more efficient than when the slice is fully immersed in culture medium according to the methods of explant culture. In addition, organotypic slice culture does not suffer from the disadvantages associated with explant-based and dissociated cell-based primary cultures discussed above. There are many examples of organotypic culture of slices of other tissues based on the same principles.

Organotypic slice culture is significantly faster and more flexible than organ culture, but it is still too slow and expensive for the large-scale screening needed for drug discovery. The procedures used to dissect organs from animals or to process post-operative human material are labour-intensive, and it is possible to carry out only tens of cultures in parallel in most laboratories. For drug screening, it would be far more useful to provide thousands, tens of thousands or hundreds of thousands of cultures in parallel. Thus the ideal method for organotypic culture would be one that was based on dissociated cells or small aggregates of cells from a particular organ, but allowed truly organotypic culture.

Surprisingly, it has been found that it is possible to produce an organotypic culture from dissociated cells or from small aggregates of cells (microexplants or explants) on a membrane by compacting them. The contralateral side of the membrane is supplied with nutrients in accordance with the teaching of Stoppini L. et al, 1991. The method of producing an organotypic culture using dissociated cells or microexplants is described in the applicant's co-pending applications entitled "Method", filed in the United Kingdom on 15 Jun. 2005 (GB0512214.8) and internationally on 15 Jun. 2006, which are incorporated herein by reference.

One aspect of both organotypic slice culture and organotypic culture from dissociated cells or microexplants is that the slice or compacted cells are placed on a porous membrane, and are provided with liquid nutrient medium from the contralateral side of the porous membrane so that the tissue or cell cultures are at the gas-liquid interface. There are devices currently available which satisfy these requirements. For example, the Millicell-CM inserts with Biopore membrane manufactured by Millipore Corporation consist of a porous membrane sealed to a polystyrene holder. The polystyrene holder surmounted by the membrane is placed in a Petri dish containing liquid medium such that the lower surface of the membrane is in contact with the liquid medium and the organ slice is placed on the upper surface of the porous membrane (see Millipore Technical Note 062).

However, the devices available for organotypic culture in the prior art have a number of disadvantages and do not provide optimum conditions for organotypic culture. For example, the devices that are currently available do not allow medium to be added to the side of the porous membrane contralateral to the cell mass after the addition of the cell mass to the porous membrane, nor do they allow for the medium to be changed. It would be useful to be able to specify individually the culture medium feeding each culture and to change each culture medium independently to assess the effects of medium change on the culture. Such medium change would need to be carried out without subjecting the organotypic culture on the surface of the porous membrane to significant changes in hydrostatic pressure, because such changes induce stretch and stress responses in cell cultures that could confound the results of biological tests. Furthermore, the devices which are currently available do not allow high throughput, i.e. they cannot be used to produce, maintain and screen multiple organotypic cultures in parallel.

There is therefore a need for a device for the preparation and maintenance of organotypic cultures that is designed to facilitate medium change without subjecting the organotypic culture to unnecessary stress and which is designed to facilitate high-throughput production and screening of the organotypic cultures.

SUMMARY OF THE INVENTION

According to a first aspect of the invention, there is provided a device for organotypic culture, said device comprising:
  a conduit having one open end and one end closed by a porous membrane fused across it; and
  a frame holding the conduit in a substantially vertical orientation;
  wherein the conduit is adapted to permit retention by capillarity of a sufficient volume of liquid culture medium in the conduit to contact the surface of the porous membrane and thus supply nutrients to cells that may be grown on the porous membrane.

During organotypic culture, the culture is maintained on the surface of the porous membrane that is disposed at one end of the conduit. One key feature of the present invention is that the conduit is designed such that, during organotypic culture, the force of capillarity maintains contact between the surface of the porous membrane contralateral to the cell culture, i.e. the surface of the membrane in the conduit, and the culture medium.

The use of the force of capillarity to maintain the culture medium in the conduit enables the removal and replacement of the culture medium by a pipetting step. When supplying the medium, the pipette tip should be positioned as closely as practicable to the surface of the membrane.

Preferably, the conduit is adapted such that it retains a sufficient volume of liquid culture medium by capillarity to maintain contact between the surface of the porous membrane in the conduit and the culture medium when the device is in either the upright or inverted position. Said conduit may be referred to herein as the medium conduit.

By upright position is meant that the frame holds the conduit substantially vertically with the end sealed by the porous membrane positioned uppermost so that, when the device is in use, the organotypic culture is grown on the upper surface of the membrane. By inverted position is meant that the frame holds the conduit substantially vertically with the open end positioned uppermost and the end closed by the porous membrane lowermost so that, when the device is in use, the organotypic culture in the lower surface of the membrane. In contrast to the devices that are available in the art, the device of the invention thus allows incubation of the organotypic culture and change of the medium for the organotypic culture with the device in either the upright or inverted position. This flexibility in orientation of the culture and the device means that either microscopes with their objective lenses facing upwards or microscopes with their objective lenses facing downwards can be used interchangeably for studying the culture, and that liquid handling devices can be used in either orientation to add or remove the medium.

Preferably, the conduit is a cylinder. The conduit may also be of rectangular or asymmetrical cross-section. The exact dimensions and composition of the conduit are selected such that, during organotypic culture, it retains a sufficient volume of liquid culture medium by capillarity to maintain contact between the surface of the porous membrane in the conduit and the culture medium, preferably irrespective of whether the device is in the upright or inverted position. The volume of liquid retained should be sufficient such that in use, adequate nutrients are supplied to the organotypic culture without requiring the medium to be changed at unreasonably short intervals.

Capillarity is dependent on several parameters. The force of capillarity is an inverse function of the diameter of a cylindrical vessel or the width or breadth of a conduit of rectangular section. The force of capillarity on an aqueous solution also depends on the surface tension of the solution being held by that force which can be weakened by the presence in solution of surfactants such as detergents. Capillarity is affected by the degree of attraction between the molecules of the liquid and the molecules of the surface. In the case of an aqueous liquid, capillarity is affected by the degree of hydrophilicity of the surface of the conduit. A further factor affecting the retention of liquid culture medium in a conduit is the volume of the culture medium. These factors therefore need to be taken into account to ensure that the device of the invention can retain a volume of liquid media in contact with the surface of the porous membrane by capillarity.

In the device of the present invention, two different capillary forces act to retain the liquid medium in the conduit in contact with the porous membrane. The force of capillarity exerted by attraction between the liquid medium and the tube is one force. The other force is exerted by attraction between the liquid medium and the walls in the pores of the membrane. If sufficiently strong, the former will counteract gravity to keep the liquid in the conduit irrespective of whether it is upright or inverted, and the latter will keep the liquid in contact with the membrane. At a certain threshold, the force of gravity on the culture medium will exceed the force of capillarity and culture medium not restrained by an additional force will fall from the conduit.

Where the conduit is a cylinder, the mass of the liquid contained in the cylinder and thus the gravitational force acting to remove the liquid from the cylinder is directly proportional to the square of the radius of the cylinder, whereas the capillary force acting to retain the liquid in the cylinder is inversely proportional to the radius. Thus for a given liquid and cylinder length there is a maximum radius above which the liquid in a cylinder of a given surface composition will not be retained against the force of gravity, but there is no minimum radius below which liquid will not be retained against the force of gravity.

Preferably, the conduit is a cylinder having a radius of 0.5 cm or less, preferably 0.3 cm or less, preferably 0.25 cm 0.2 cm, 0.15 cm or less. Preferably, the cylinder has a radius of approximately 0.3 cm, 0.15 cm or 0.075 cm. It has been found that cylindrical conduits having a radius of 0.5 cm or less are adapted to maintain a 1 cm column of a standard liquid culture medium, such as Dulbecco's Minimum Essential Medium, in contact with the surface of the porous membrane in the conduit, irrespective of whether the device is in an upright or inverted position. Preferably, the conduit, preferably a cylinder, is about 1 cm in length, to allow it to retain a 1 cm column of liquid. Preferably, the conduit is slightly greater than 1 cm in length, preferably approximately 1.1 cm or 1.2 cm in length.

Preferably, the conduit is made of a hydrophilic material, preferably a hydrophilic polymer, to increase the force of capillarity exerted on the liquid medium when it is in the conduit. Hydrophilic polymers will be known to the person skilled in the art. The hydrophilicity of polymers from which the conduit is made may be increased further, for example by inclusion of polyethylene glycol groups.

Figure 6:
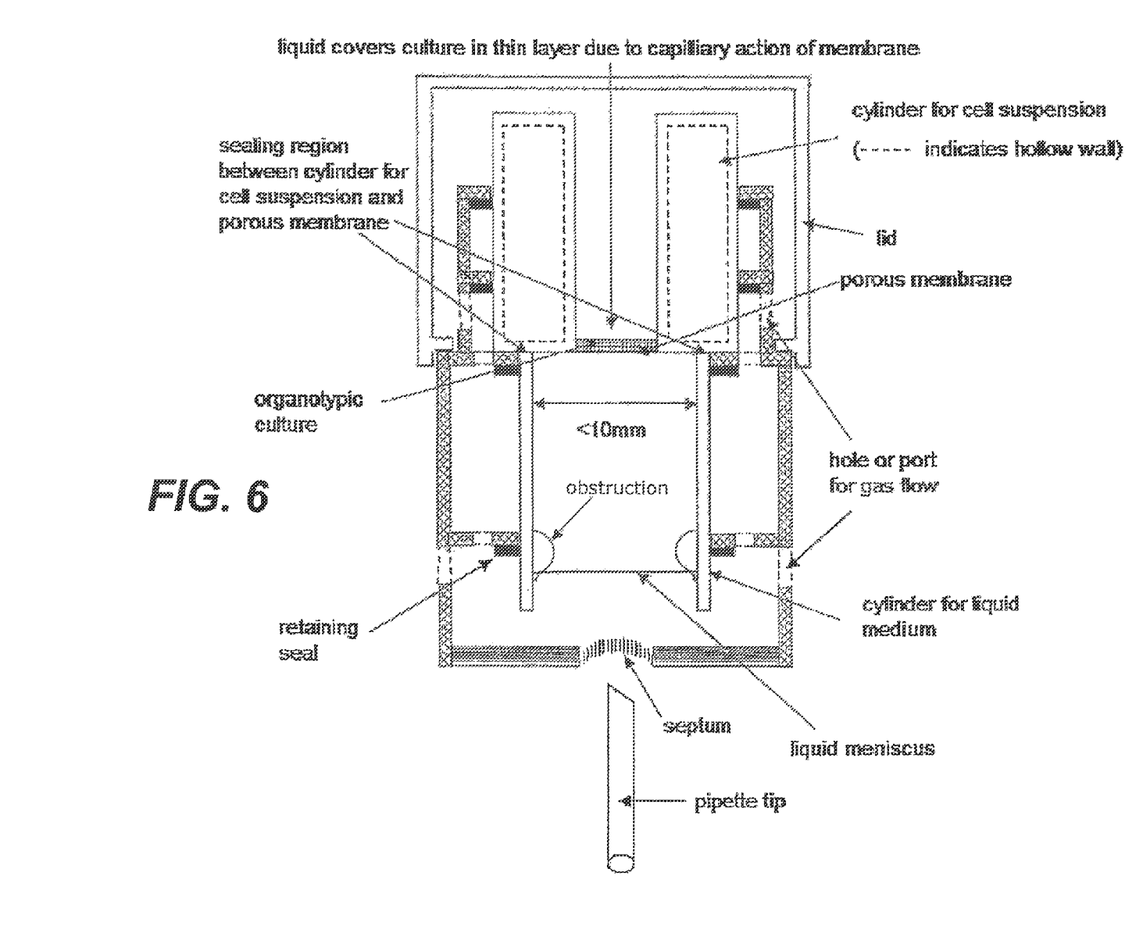
FIG. 6 illustrates a generic obstruction in a medium conduit.

The invention is not limited to cylinders with a radius of less than 0.5 cm as it will be well within the skilled person's ability to determine the dimensions of other conduits which may be used in the device. Specifically, the skilled person will be able to calculate the forces of capillarity and gravity exerted on a given volume of liquid culture medium in conduits of different dimensions and thus determine what dimension of conduit should be employed in the device to ensure that the forces of capillarity exceed the forces of gravity such that the liquid is retained in the conduit. Furthermore, constrictions, platforms or other obstructions (see FIG. 6) may be included in the conduit to increase resistance to the force of gravity acting to remove the medium from the conduit.

According to the Laplace-kelvin equation, $$\text{force of capillarity} = \text{surface tension}/(R1-R2),$$

where R1=the radius of the tube or pore (in this case the conduit) in cm and R2=the thickness of the meniscus layer in contact with the wall of the tube or pore.

1 dyne is the force required to accelerate 1 gram at 1 cm $\sec^{-2}$. The surface tension of an aqueous medium is about 73 dyne $\text{cm}^{-2}$ unless surfactants such as detergents are included. It is not common practice to include detergents in culture media but proteins can also affect surface tension and proteins are commonly included in media particularly in the form of serum. Generally, the surface tension of a liquid culture medium is at least 50 dyne $\text{cm}^{-2}$. The total force of gravity acting on a given volume of liquid culture medium is 98× (volume in $\text{cm}^3$) dyne. The thickness of the meniscus layer (R2) generally need not be taken into consideration when calculating capillarity for the purpose of the present invention. When R2 is small, it has a negligible effect on capillarity and as R2 approaches R1, the capillary force becomes greater. As it is only necessary to determine whether the minimum capillary force requirements are met for a given conduit and aqueous medium for the purpose of the present invention, measurement of R2 is not therefore necessary. It is, however, of course possible to measure R2 if it is desired to calculate the force of capillarity more precisely.

For a cylinder of length 1 cm and a radius of 0.5 cm, a total capillary force of at least 77 dyne would therefore be required to counteract the force of gravity and maintain a 1 cm column of liquid with surface tension 50 dyne $\text{cm}^{-2}$ in the cylinder by capillarity when inverted. If the hydrophilicity of the cylinder surface is sufficiently high, the force of capillarity can apply a force of greater than 100 dyne to such a column of liquid.

For a cylinder of length 1 cm and a radius of 0.3 cm, a total capillary force of at least 28 dyne would be required to counteract the force of gravity and maintain a 1 cm column of liquid with surface tension 50 dyne $\text{cm}^{-2}$ in the cylinder when inverted. If the hydrophilicity of the cylinder surface is sufficiently high, the force of capillarity can apply a force of greater than 170 dyne to such a column of liquid.

These forces of capillarity are sufficient to retain such a column of liquid when inverted provided that the device is not moved or vibrated, because accelerations caused by movement or vibration change the momentum of the column of liquid and can overcome the restraining force. Preferably, the dimensions of the conduit are such that no reasonable changes in momentum such as may be caused by normal manual or robotic manipulations result in the loss of liquid from the conduit.

Preferably, the dimensions of the conduit are selected such that the capillary force acting to retain a given volume of liquid medium at the surface of the porous membrane is at least 6 times the gravitational force acting to release the medium. A capillary force of 6 times the gravitational force has been found to be adequate to ensure retention of liquid media in the conduit of the device under normal handling, even when the medium contains protein components such as those in serum that diminish the surface tension of the medium.

Preferably, the porous membrane is fused across one end of the conduit by gluing, by heat-sealing or by ultra-sonic sealing. The porous membrane applies a capillary force to the liquid in the conduit according to the Laplace-Kelvin equation (see above), depending on the radius and surface composition of the pores in the membrane. This capillary force exerted by the membrane should be sufficient to wet the membrane and keep the liquid in contact with the membrane.

Preferably, the porous membrane in the device of the invention comprises pores with a size of ~0.4 µm. Membranes suitable for use in the device of the invention include but are not limited to the hydrophilic polytetrafluoroethylene (PTFE, also known under the DuPont trade name Teflon®) membrane produced by Millipore Corporation which is optically transparent, membranes made of polycarbonate, PET (polyethylene terephthalate), or Anopore™ (inorganic aluminium oxide, a trademark of Whatman Corp).

Preferably, the porous membrane is optically transparent. This feature enables the test cultures to be accessible at all times to microscopic examination and sampling for biochemical assays. Preferably, the porous membrane produces low background fluorescence at the wavelengths used for excitation, usually in the range of 400-750 nm. Preferably, the porous membrane is composed of hydrophilic polytetrafluoroethylene (PTPE) membrane.

Preferably, the frame holds the conduit in a vertical orientation such that neither the end of the conduit closed by the membrane nor the open end of the conduit is in contact with any surface. Preferably, the device further comprises a sealing ring which ensures that the frame is held firmly in contact with the conduit. Preferably, the device comprises two such sealing rings. The device may further comprise additional means to ensure that the frame is held firmly in contact with the conduit so that the conduit is not released when it is inverted. Such additional means may comprise, for example, friction means such as springs between the frame and the conduit.

Preferably, the device further comprises a chamber enclosing the open end of the conduit. The chamber may form part of the frame holding the conduit in a vertical orientation. When the device is in use, the chamber contains an atmosphere of suitable gaseous composition that contacts the medium in the conduit to maintain optimum acidity and oxygen levels in the medium. The chamber is preferably sealed to ensure that the liquid medium is not exposed to the external atmosphere during use. The chamber may further comprise a gas inlet and a gas outlet to allow control of the atmospheric conditions in the chamber.

Preferably, the sealed chamber further comprises an opening to allow the culture medium to be changed. Preferably the opening is designed to minimise exposure of the culture medium to the atmosphere when the medium is changed. The opening may be sealed by a septum or valve that it is normally sealed but may be penetrated by a pipette tip to withdraw the medium and introduce new medium. The septum may be made of rubber or neoprene. The opening may also be used to introduce specific components to the existing medium, such as growth factors or antibiotics or toxins, rather than to change the medium completely. Preferably, the pipetting step is conducted without subjecting the culture to a significant change in hydrostatic pressure.

It will be apparent to those skilled in the art of manual and robotic pipette construction that to withdraw liquid from the conduit, a negative pressure must be applied that is greater than the pressure retaining the liquid in the conduit. It will be important to avoid damage by the pipette tip to the porous membrane, and for this reason the pipette tip will not be advanced into contact with the said membrane. It may not therefore be possible to remove all the liquid medium from a conduit with a single pipetting step. Liquid may be retained in the conduit in the region of the conduit between the point of furthest travel by the pipette tip and the membrane. Such retention of liquid in the conduit by capillary force is most likely to apply with very small cylinder radius, although it will also depend upon the precise properties of the pipette tip and the liquid. If retention of liquid does occur, it will not, in most cases, affect the health of the culture.

In some circumstances, however, for example if exposure of the culture to a toxic substance is being tested, retention of liquid could potentially influence experimental data. In this case the pipetting steps of liquid removal and replacement with fresh liquid may be repeated as many times as necessary to remove the toxic substance by dilution. For example, if the cylinder is 1 cm long and the pipette tip can be safely advanced to within 0.1 cm of the membrane, then at most 10% of the volume may be retained in the cylinder. The addition of fresh liquid to the full 1 cm length would dilute the toxin to 10% of its original concentration. Repetition of this process would dilute the toxin to 1% of its original concentration. The time programming of pipetting steps would take into account the need to allow equilibration of the toxin to maximise the efficiency of removal by dilution.

Preferably the device further comprises one or more conduits preferably removable conduits to contain the cells prior to and during compaction by a gravitational field, such conduits or removable conduits placed on the contralateral side of the membrane to the conduit that contains the culture medium. The device of this embodiment allows compaction of the cells by centrifugation and transfer of the cells to the surface to be carried out simultaneously. A conduit is provided to hold the cell suspension in the correct orientation with respect to the surface for compaction by a gravitational field. The optimum orientation is with the surface distal to the cell suspension from the point of minimum gravitational field strength. In the case of a gravitational field generated within a centrifuge, the surface is placed distal to the axis of rotation of the centrifuge rotor compared to the cell suspension. Preferably at the junction of the conduit and the surface is provided a seal between the surface and the edge of the conduit that is adjacent to the said surface, to ensure that the cells are transferred efficiently to the said surface and not lost from the conduit. After compaction of the cells by centrifugation, liquid medium is transferred to the conduit provided to contain the medium on the contralateral side of the porous membrane to the conduit provided to contain the cell suspension. Further compaction of the cells then occurs by capillarity. The conduit that contains the cell suspension is called the cell suspension conjugate herein, and the conduit that contains the liquid medium is called the medium conduit. The use of more than one cell suspension conduit prior to and during compaction enables more than one culture to be established on different sites within the region of the membrane in contact with each medium conduit. If the cell suspension conduits are not removable, they may be sealed permanently to the porous membrane by gluing or by heat-sealing or by ultra-sonic sealing. If the cell suspension conduits are removable they are sealed to the porous membrane non-permanently. Examples of non-permanent seals include shaped edges that focus pressure and silicone and other compressible substances which may comprise all of the conduit or the sealing edge of the conduit. It will be appreciated by those familiar with centrifugation that the application of a gravitational field to a device including a conduit proximal to the porous membrane with respect to the axis of rotation of the centrifuge rotor will press the sealing edge of the conduit against the porous membrane. In the case of a removable conduit this enhances the sealing properties of the sealing edge. It will also be appreciated by those skilled in the art of design of devices for use in gravitational fields that load-bearing surfaces must be supported by structures of adequate strength to avoid failure. For example, the porous membrane of the invention does not have adequate strength to support a conduit in even a weak gravitational field without damage to the porous membrane. Therefore steps have been taken to ensure that the conduits of the invention are supported by structures of adequate strength within the frame of the device. If a compressible seal is used between a conduit and a porous membrane, the degree of compression under the influence of a gravitational field is in all cases limited by contact of the conduit with a structure of adequate strength within the frame of the device. These considerations are obvious to those skilled in the art of design of devices for use in gravitational fields.

Accordingly, the invention preferably comprises a cell suspension conduit having one end open and one end closed by the surface of the said porous membrane contralateral to the surface of said porous membrane sealed to the said medium conduit. The frame then preferably holds the medium conduit and the cell suspension conduit in a substantially vertical orientation Preferably, the device further comprises a lid that covers the surface of the porous membrane outside the conduit. The lid covers the surface of the porous membrane on which the culture is located when the device is in use. Where the device comprises a lid, the chamber and the frame preferably comprise additional ports to allow gas flow between the chamber and space above the membrane enclosed by the lid, allowing the atmosphere surrounding the culture to be controlled over periods of several weeks or more.

The device of the first aspect of the invention is preferably adapted for use in high-throughput methods that involve preparing and maintaining multiple organotypic cultures simultaneously. According to a second aspect of the invention, there is therefore provided a device for high-throughput organotypic culture comprising multiple devices according to the first aspect of the invention. Preferably, the device for high-throughput organotypic culture comprises 96, 384, 1536 or more devices according to the first aspect of the invention.

The device of the second aspect of the invention may thus contain thousands of medium conduits, and in some embodiments thousands of cell suspension conduits, and each medium conduit can be supplied independently with culture medium and for which the culture medium can be changed independently. Preferably, the medium change is carried out by a multichannel pipette or robot as described above.

Preferably, the high-throughput device comprises a single lid covering all of the individual conduits within the device.

Preferably, the chambers enclosing the open ends of each medium conduit in the high-throughput device are connected by an opening, allowing gas flow between the chambers so that gas flow to all of the chambers within the device may be controlled by a single gas flow inlet and outlet in the high-throughput device.

The multiple devices in the high-throughput device may be fabricated as a single unit. Alternatively, the high-throughput device may be supplied as individual devices according to the first aspect of the invention each containing a single medium conduit and in some embodiments one or more permanent or removable cell suspension conduits that can be assembled into a high-throughput device containing the desired number of conduits by the user. The high-throughput device may also be supplied as strips of individual devices according to the first aspect of the invention, for example, in batches of 2, 4, 8, or 12, that can be assembled into a high-throughput device containing the desired number of conduits, optionally by the user. High-throughput devices comprising strips containing a set number of wells are known in the art for cell culture, although not for organotypic culture. A multiwell device of this type has been described by Dynatech in Thorne A. (1979) in U.S. Pat. No. 4,154,795.

Preferably, for high-throughput devices, the overall size of the device and the position of the individual conduits within the device should match the size of a standard microtitre plate to enable the device to be use with robotics designed for standard microtitre plates. For example, in a high-throughput device comprising 96 devices according to the first aspect of the invention, the devices are preferably arranged in an array of 8 by 12 devices, resembling a standard 96 well microtitre plate. The conduits in the 96 devices making up the high-throughput device are preferably cylinders. Preferably each cylinder comprising a medium conduit has a radius of approximately 0.3 cm which is the radius of a well in a standard 96 well microtitre plate. The capilliary and gravitational forces acting in such a cylinder have been described above. The dimensions of the cell suspension conduits are not limited by the need to retain liquid by capillarity against the force of gravity, because they are always used with the porous membrane at the point of maximum gravitational field strength. Preferably each cylinder comprising a cell suspension conjugate can be filled and aspirated simply by pipetting devices designed for standard microtitre plates. For example if the device contains one cell suspension conduit for each medium conduit and there are 96 medium conduits, the axis of each cell suspension conduit should optimally be co-linear with the axis of the medium conduit placed directly opposite on the contralateral side of the porous membrane. If the device contains 4 cell suspension conduits for each of 96 medium conduits, the spacing of the cell suspension conduits should be equivalent to the wells of a 384 well microtitre plate. If the device contains 16 cell suspension conduits for each of 96 medium conduits, the spacing of the cell suspension conduits should be equivalent to the wells of a 1536 well microtitre plate. The radius of each cell suspension conduit should be sufficiently greater than the radius of a suitable pipette tip or pipette needle to allow convenient pipetting.

In a high throughput device comprising 384 devices according to the first aspect of the invention, the medium conduit in each device is preferably a cylinder and the cylinder radius is preferably approximately 0.15 cm, the radius of a well in a standard 384 well microtitre plate. The weight of the liquid in this cylinder of the same 1 cm length is only 25% of the corresponding weight with a cylinder diameter of 0.3 cm, but the capillary force is doubled compared to the aforesaid larger cylinder. In a high throughput device comprising 1536 devices according to the first aspect of the invention, the medium conduit in each device is preferably a cylinder and the cylinder radius is preferably approximately 0.075 cm, the radius of a well in a standard 1536 well microtitre plate. In this case the weight of liquid in the cylinder of the same 1 cm length is only 6.25% of the corresponding weight with a cylinder diameter of 0.3 cm, but the capillary force is fourfold higher. In a high throughput device comprising 96, 384 or 1536 medium conduits there can be one or more cell suspension conduits for each medium conduit, the number and positioning of the said cell suspension conduits being limited only by the ability to use suitable instruments for high throughput pipetting. Thus, devices of 96, 384 or 1536 medium conduits made according to the invention to the overall size of a standard microtitre plate all retain liquid in the medium conduits in the inverted position, and all can contain permanent or removable cell suspension conduits.

Various aspects and embodiments of the present invention will now be described in more detail by way of example. It will be appreciated that modification of detail may be made without departing from the scope of the invention.

EXAMPLES

Figure 1:
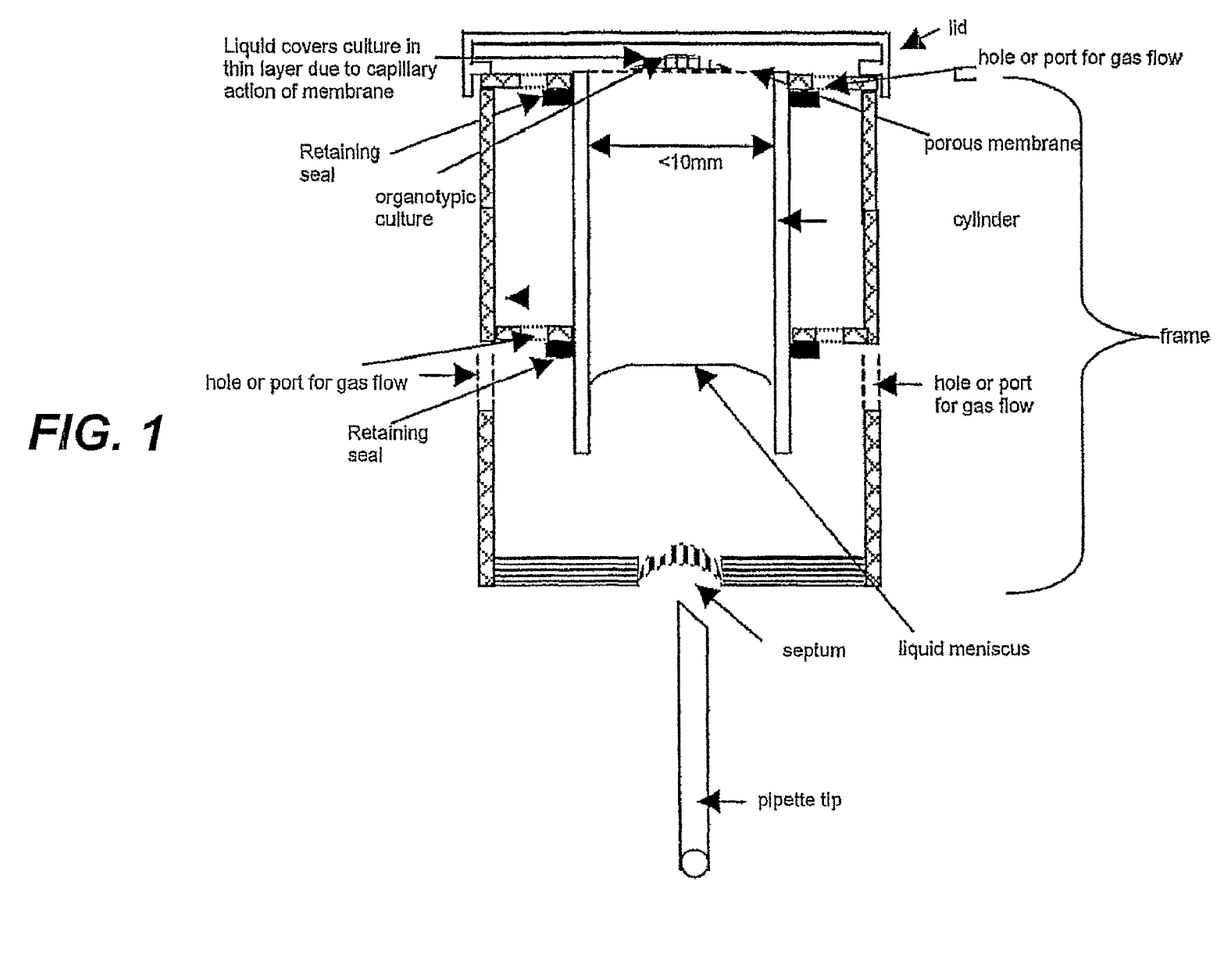
FIG. 1 shows a cross-section of a device without a cell suspension conduit according to the first aspect of the invention.

As shown in FIG. 1, a preferred device of the invention comprises a cylinder as a medium conduit and a porous membrane glued or heat-sealed or ultrasonically sealed to one end of the cylinder, and a frame which holds the cylinder vertically and creates a chamber surrounding the open end of the cylinder.

The cylinder contains a volume of liquid culture medium which is retained by capillarity in the cylinder so that it is in contact with the lower surface of the porous membrane. The liquid meniscus of the volume of liquid medium is shown.

Figure 2:
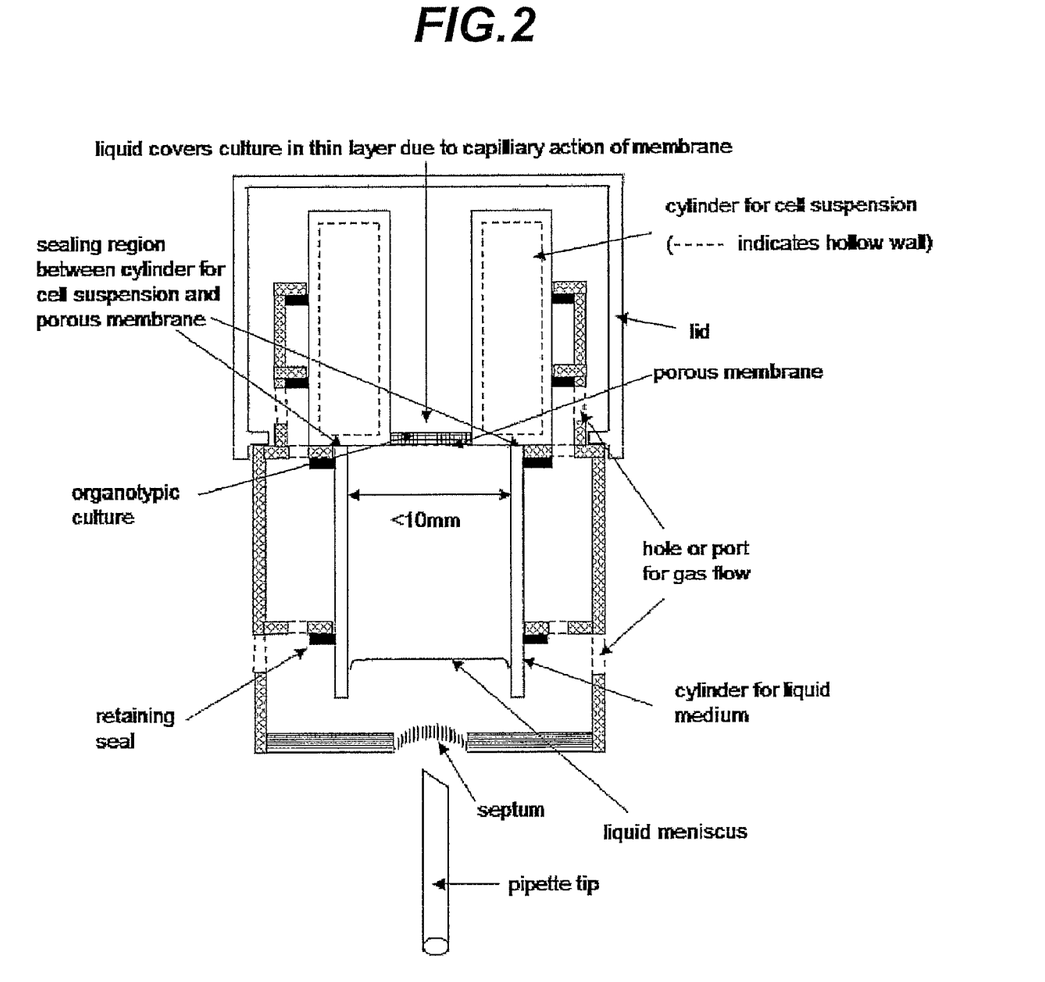
FIG. 2 shows a cross-section of a device with a cell suspension conduit according to the first aspect of the invention.

As shown in FIG. 2, a further preferred device of the invention comprises a cylinder as a medium conduit and a porous membrane glued or heat-sealed or ultrasonically sealed to one end of the medium conduit, and a further cylinder as a cell suspension conduit that is sealed to the contralateral side of the porous membrane to the medium cylinder, and a frame which holds both cylinders vertically and creates a chamber surrounding the open end of the medium conduit cylinder.

The cell suspension conduit cylinder contains cell suspension prior to and during compaction by centrifugation. The cell mass obtained following centrifugation is shown. Following centrifugation, the medium conduit cylinder contains a volume of liquid culture medium which is retained by capillarity in the cylinder so that it is in contact with the lower surface of the porous membrane. The liquid meniscus of the volume of liquid medium is shown.

The devices of FIGS. 1 and 2 further comprise a lid which encloses the membrane-sealed end of the vessel and provides for control of the atmosphere surrounding the organotypic culture, in that gaseous exchange is possible, but microbial contamination is prevented.

In the case of an assembly of devices for high throughput the lid preferably would cover the whole assembly. The lid may be loose-fitting to allow gas diffusion, having a skirt that overlaps the edges of the dish or the assembly to minimise contamination in the presence of slight air turbulence. It is well known by practitioners of tissue culture that air turbulence should be minimised. Alternatively, the lid may be tight fitting in which case ports may be provided in the frame so that gas can circulate between the chambers and the space between the lid and the membrane.

The chamber preferably comprises a pre-fabricated plastic shape incorporating two sealing rings which position the chamber firmly around the base of the medium conduit cylinder. Additionally, if a cell suspension conduit cylinder is present, two sealing rings are used to position the cell suspension conduit cylinder within the prefabricated plastic shape. Preferably, the seals are sealing rings fabricated of neoprene. Preferably the cell suspension conduit cylinder is fabricated of silicone, a semi-rigid material, to ensure sealing against the porous membrane during centrifugation.

The base of the chamber further comprises a septum which can be penetrated by a pipette to facilitate change of the medium in the chamber without exposing the medium to the surrounding environment.

The interior of the chamber preferably is accessible for gas diffusion or perfusion and the chamber comprises two holes or ports for gas flow to control atmospheric conditions. The chamber and the frame preferably comprises additional ports to allow gas flow between the chamber and the space above the membrane covered by the lid.

Figure 3:
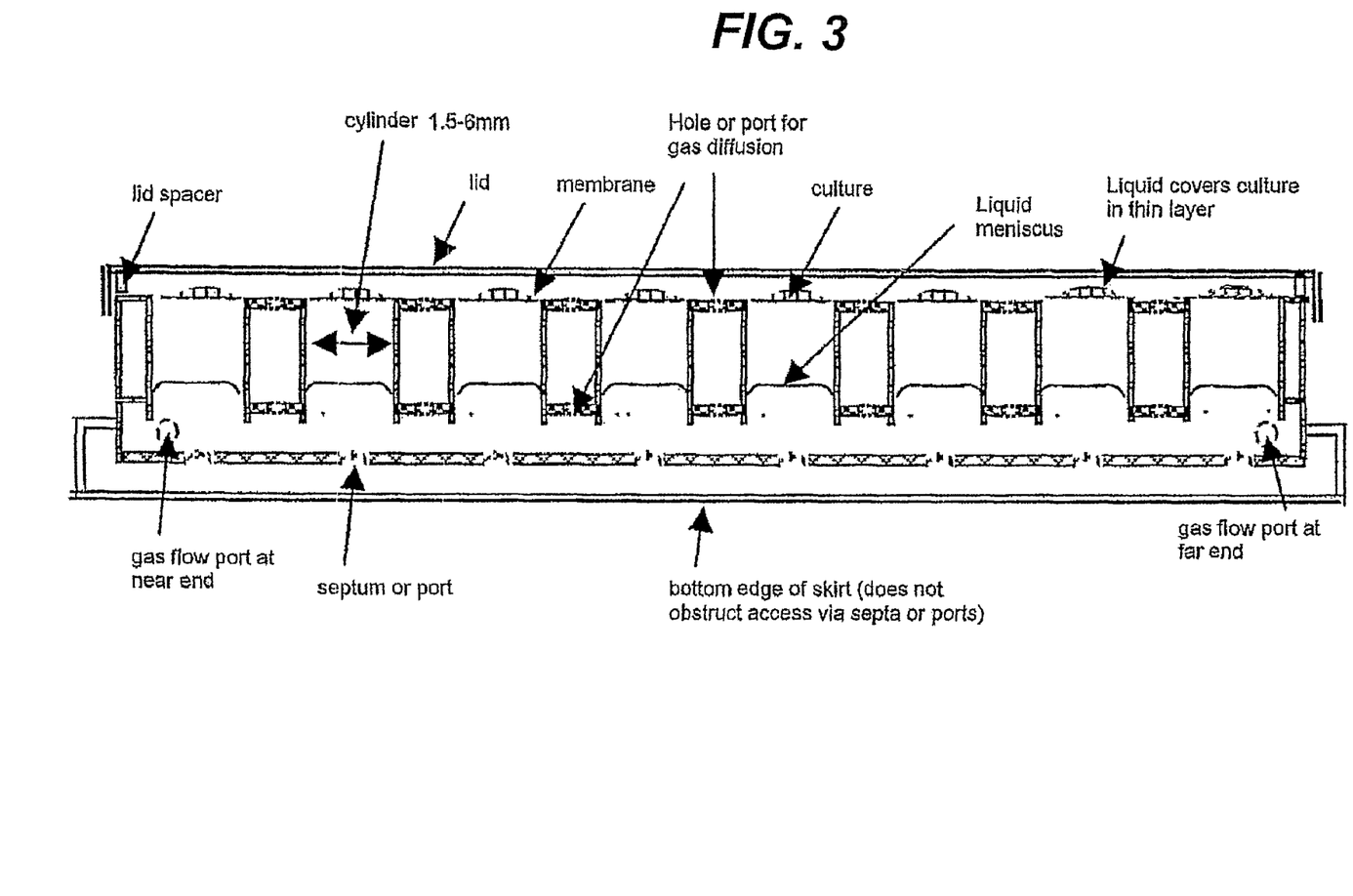
FIG. 3 shows a cross-section of a high throughput device without cell suspension conduits for organotypic culture according to the second aspect of the invention.
Figure 4:
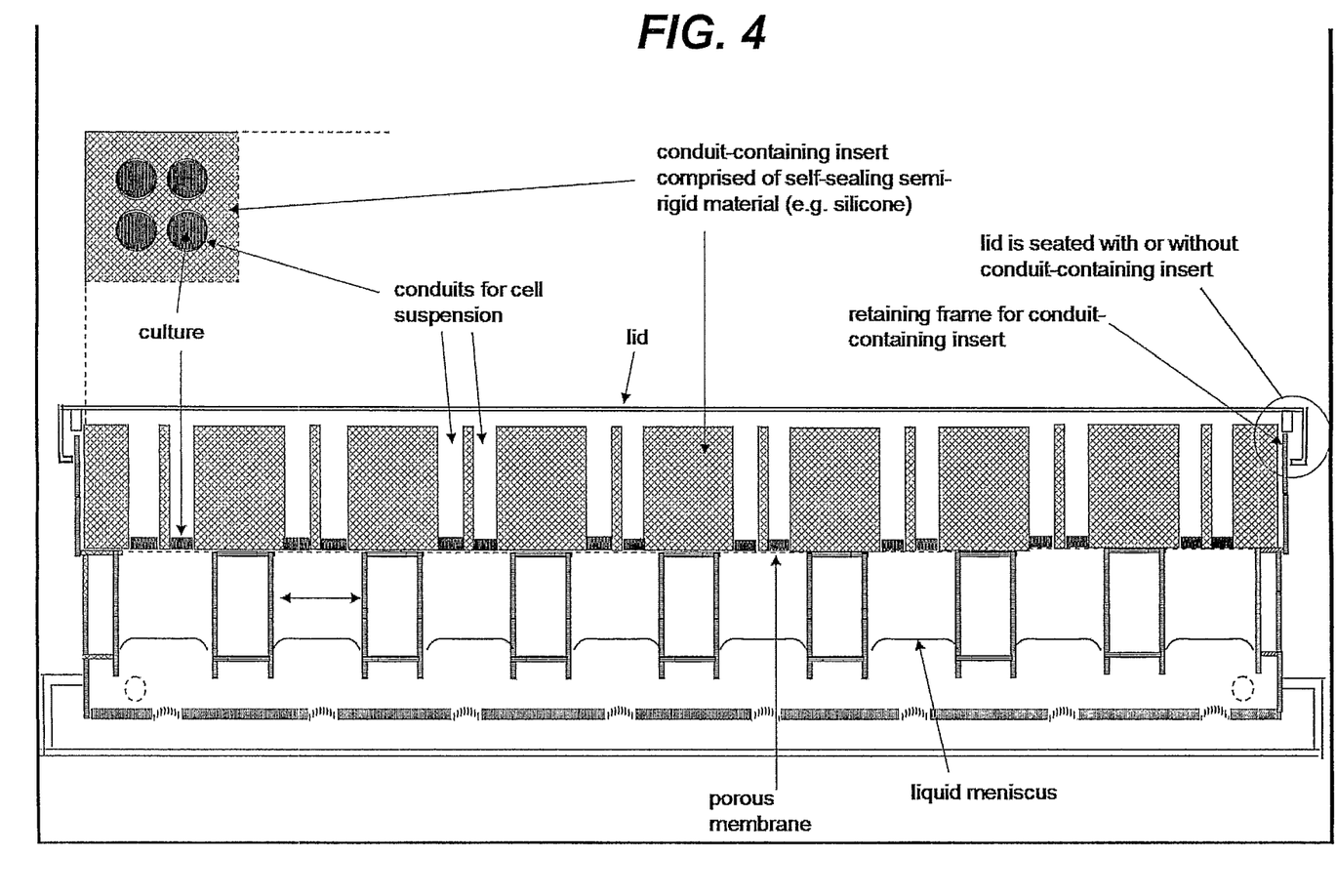
FIG. 4 shows a cross-section of a high throughput device and removable conduits for a high throughput device including 4 conduits per well for containing cells before and during compaction.

As shown in FIG. 3, a high throughput device for multiple organotypic cultures according to the invention comprises multiple devices for a single organotypic culture shown in FIG. 1. Each medium conduit cylinder in the high-throughput device contains its own supply of liquid medium retained in contact with the membrane by capillarity. As shown in FIG. 4, a further high throughput device for multiple organotypic cultures according to the invention comprises multiple devices for organotypic culture shown in FIG. 2. Each medium conduit cylinder in the high-throughput device contains its own supply of liquid medium retained in contact with the membrane by capillarity. Corresponding to each medium conduit cylinder, there are one or more cell suspension conduit cylinders which contain the cell suspension before and during centrifugation. In the example shown in FIG. 4 there are four cell suspension conduit cylinders, and so four organotypic cultures, for each medium conduit cylinder.

The chambers at the base of the medium conduit cylinders in FIGS. 3 and 4 are in communication, and gas flow between the chambers is possible, thereby allowing the control of atmospheric conditions in all the chambers through the gas flow ports at either end of the device. Furthermore, the space between the lid and the culture is made contiguous with the chambers by means of ports in the frame, thereby allowing control of the atmospheric conditions surrounding the cultures on the membranes.

Figure 5:
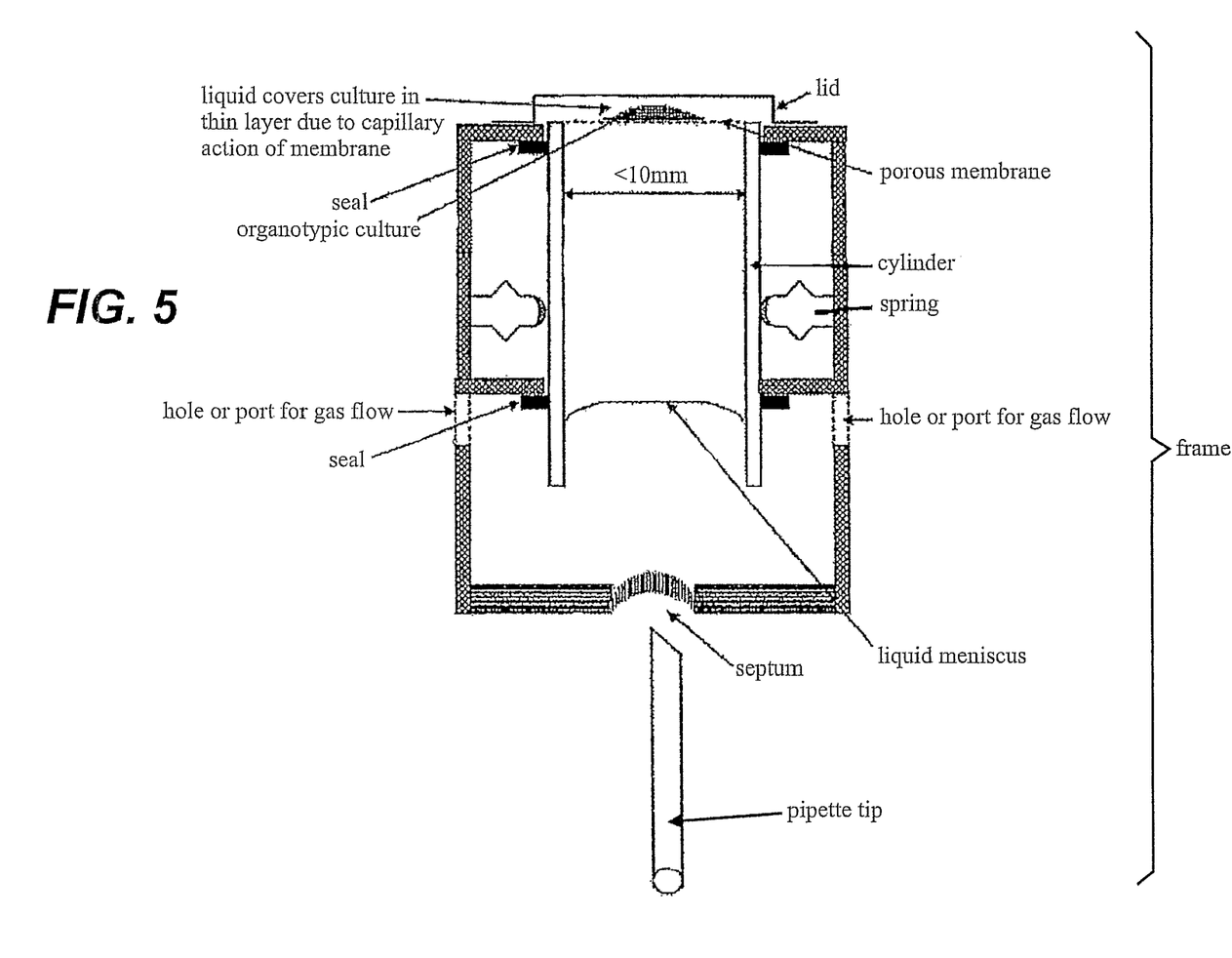
FIG. 5 shows a cross-section of a modified device for organotypic culture according to the first aspect of the invention with additional components holding the conduit in place.

As shown in FIG. 5, the devices of FIGS. 1 and 2 may comprise further elements that hold the conduit in place relative to the frame such as, for example, springs between the conduit and the frame.

REFERENCES

Corradino R., 1973, J. Cell Biol., Vol 58, pp 64-78, Embryonic click intestine in organ culture. A unique system for the study of the intestinal calcium absorptive mechanism.
Stoppini L. et al, 1991, Neurosci. Methods, Vol 37 pp 173-82, A simple method for organotypic cultures of nervous tissue.
Wicks W., 1968, J. Biol. Chem., Vol 243, pp 900-6, Induction of tyrosine-alpha-ketoglutarate transaminase in fetal rat liver.
Wildenthal K., 1971, J. Appl. Physiol., Vol 30, pp 153-7, Long-term maintenance of spontaneously beating mouse hearts in organ culture.

The invention claimed is:

1. A device for organotypic culture, said device comprising:
   first and second medium conduits, each having one open end and one end closed by a porous membrane fused across it; and
   a frame holding at least the first medium conduit in a substantially vertical orientation
wherein each of the first and second medium conduits is adapted to permit retention by capillarity of a sufficient volume of liquid culture medium in the medium conduit to contact the surface of the porous membrane and thus supply nutrients to cells that may be grown on the porous membrane when the device is in either the upright or the inverted position,
wherein the device further comprises
   a cell suspension conduit having one end open and one end closed by the surface of said porous membrane contralateral to the surface of said porous membrane sealed at least to said first medium conduit;
   wherein said frame holds at least the first medium conduit and the cell suspension conduit in a substantially vertical orientation
   wherein the device further comprises a chamber enclosing the open end of at least the first medium conduit; wherein the chamber comprises an opening to allow culture medium to be supplied independently to the first and second medium conduits.

2. A device according to claim 1 wherein at least the first medium conduit is a cylinder.

3. A device according to claim 1 wherein the cell suspension conduit is a cylinder.

4. A device according to claim 1, wherein at least the first medium conduit is a cylinder having a radius of 0.5 cm or less.

5. A device according to claim 1 wherein the porous membrane is fused across one end of at least the first medium conduit by gluing, by heat-sealing or by ultra-sonic sealing.

6. A device according to claim 1 wherein the cell suspension conduit is sealed to the porous membrane by an edge pressed against the said porous membrane by a gravitational field.

7. A device according to claim 1 wherein the cell suspension conduit is sealed to the porous membrane by a neoprene seal.

8. A device according to claim 1 wherein the cell suspension conduit is sealed to the porous membrane by a silicone seal.

9. A device according to claim 1 wherein the cell suspension conduit can be removed from the device prior to cell culture.

10. A device according to claim 1 wherein the cell suspension conduit is sealed to the porous membrane by gluing, by heat-sealing or by ultra-sonic sealing.

11. A device according to claim 1 wherein the cell suspension conduit is composed of silicone.

12. A device according to claim 1 wherein the internal cross-sectional area of the cell suspension conduit is smaller than the internal cross-sectional area of at least the first medium conduit.

13. A device according to claim 1 wherein the porous membrane is optically transparent.

14. A device according to claim 13 wherein the porous membrane is composed of hydrophilic polytetrafluoroethylene (PTFE).

15. A device according to claim 1 wherein the frame holds at least the first medium conduit in a substantially vertical orientation such that neither the end of the conduit closed by the membrane nor the open end of the conduit is in contact with any surface.

16. A device according to claim 1 wherein the frame holds at least the cell suspension conduit in a substantially vertical orientation such that the end of the cell suspension conduit in contact with the membrane is supported in a gravitational field by the said frame preventing damage to the said membrane.

17. A device according to claim 1 comprising a lid that covers the surface of the porous membrane contralateral to the liquid culture medium.

18. A device according to claim 1, wherein said device is for high-throughput organotypic culture and comprises multiple openings and cell suspension conduits.

19. A device for organotypic culture, said device comprising:
   a medium conduit having one open end and one end closed by a porous membrane fused across it; and
   a frame holding the medium conduit in a substantially vertical orientation wherein the medium conduit is adapted to permit retention by capillarity of a sufficient volume of liquid culture medium in the medium conduit to contact the surface of the porous membrane and thus supply nutrients to cells that may be grown on the porous membrane;
   wherein said medium conduit comprises an obstruction to increase resistance to the force of gravity acting to remove the medium from the conduit.

20. A device for organotypic culture, said device comprising:
   a medium conduit having one open end and one end closed by a porous membrane fused across it; and
   a frame holding the medium conduit in a substantially vertical orientation wherein the medium conduit is adapted to permit retention by capillarity of a sufficient volume of liquid culture medium in the medium conduit to contact the surface of the porous membrane and thus supply nutrients to cells that may be grown on the porous membrane when the device is in either the upright or inverted position,
   wherein the device further comprises a cell suspension conduit having one end open and one end closed by the surface of said porous membrane contralateral to the surface of said porous membrane sealed to said medium conduit;
   wherein said frame holds the medium conduit and the cell suspension conduit in a substantially vertical orientation;
   wherein the internal cross-sectional area of the cell suspension conduit is smaller than the internal cross-sectional area of the medium conduit.

21. A device according to claim 1, wherein the device comprises more than two medium conduits.

* * * * *